United States Patent [19]
Boussignac et al.

[11] Patent Number: 5,378,237
[45] Date of Patent: Jan. 3, 1995

[54] DILATATION CATHETER FOR PERFUSION

[75] Inventors: Georges Boussignac, Antony; Jean-Claude Labrune, Boulogne, both of France

[73] Assignee: Laboratoire Nycomed Ingenop SA, Paris Cedex, France

[21] Appl. No.: 842,550

[22] Filed: Feb. 27, 1992

[30] Foreign Application Priority Data

Jan. 17, 1992 [FR] France ................. 92 00499

[51] Int. Cl.⁶ .................................... A61M 29/00
[52] U.S. Cl. ................................ 604/96; 604/102; 606/194; 606/192
[58] Field of Search ............ 604/96, 102–103; 606/192, 191, 194

[56] References Cited

U.S. PATENT DOCUMENTS

| | | | |
|---|---|---|---|
| 4,795,427 | 1/1989 | Helzel | 604/53 |
| 4,892,519 | 1/1990 | Songer et al. | 604/96 |
| 4,909,252 | 3/1990 | Goldberger | 606/194 |
| 4,923,549 | 2/1988 | Wholey et al. | 606/194 |
| 5,000,734 | 3/1991 | Boussignac et al. | 604/96 |
| 5,046,503 | 9/1991 | Schneiderman | 128/692 |
| 5,078,685 | 1/1992 | Colliver | 604/96 |
| 5,085,636 | 2/1992 | Burns | 604/99 |
| 5,087,247 | 2/1992 | Horn et al. | 604/98 |
| 5,090,958 | 2/1992 | Sahota | 604/98 |
| 5,108,370 | 4/1992 | Walinsky | 604/96 |
| 5,114,423 | 5/1992 | Kaprzyk et al. | 606/27 |
| 5,137,513 | 8/1992 | McInnes et al. | 604/96 |
| 5,192,295 | 3/1993 | Danforth et al. | 606/194 |

FOREIGN PATENT DOCUMENTS

246998  11/1987  European Pat. Off. ............ 606/192

*Primary Examiner*—C. Fred Rosenbaum
*Assistant Examiner*—Corrine Maglione
*Attorney, Agent, or Firm*—Ladas & Parry

[57] ABSTRACT

The present invention relates to a dilatation catheter designed to be introduced into a canal of the body. The invention finds a particular application in the treatment of diseases of the coronary arteries. According to the invention, the balloon has an outer wall designed to come into contact with the inner wall of the body canal, while in the position of use, and an inner wall fixed in a tight manner to the outer wall to define therewith, while in the position of use, an inner annular cavity. The catheter further includes a support element shaped so as to hold the inner wall of the balloon, in the position of use, while allowing the body fluid to flow in the space between an inner element and the inner wall of the balloon.

11 Claims, 8 Drawing Sheets

Fig_1

Fig_8

Fig-9

Fig_10

DILATATION CATHETER FOR PERFUSION

FIELD OF THE INVENTION

The present invention relates to a perfusion dilatation catheter designed to be introduced into a canal of the body such as for example a blood vessel.

The invention finds an application principally in the treatment of diseased coronary arteries but it can also be used in the treatment of disorders in other canals of the body, such as for example the oesophagus or the urethra.

BACKGROUND OF THE INVENTION

These diseases are generally due to the presence, on the inner walls of the canal, of deposits which cause constriction or stenosis therein.

A catheter is generally used for treating such diseases:
on the one hand, to restore the normal flowing section of the canal in the stenosis area by compression applied by a balloon,
on the other hand, to inject, for example through the balloon wall, a treating product intended to make the restored flowing section of the canal last, if necessary by forming in situ a prosthesis of corresponding section.

Normally, during the compression (crushing of the deposits with the balloon), the canal is entirely obturated by the balloon. Yet, it is necessary, during the intervention, to keep up a minimum flow of fluid in the canal, in order to prevent any risks of damage to the tissues or organs situated downstream of the balloon.

Various solutions have been proposed in the prior art in order to solve this problem.

For example, in U.S. Pat. Nos. 4,771,777, 4,790,315 or 4,892,519, it has been proposed to make the body fluid flow through the inner tabular member of the dilation catheter through which passes the guide.

This solution, however, is not satisfactory in that the body fluid flowing section is limited, on the one hand, because of the small diameter of the inner tubular member, and on the other hand, because of the presence of the guide.

In U.S. Pat. No. 5,000,734, it is proposed to make the body fluid flow through the balloon. To this effect, the balloon comprises, when in the inflated state, a plurality of longitudinal conduits.

This solution which constitutes an improvement over that described in the aforecited documents, is not altogether satisfactory.

Indeed, as it appears, the body fluid flowing section is dependent on the number and diameter of the conduits provided on the balloon.

Yet, such conduits are relatively difficult to produce and too high a number of them would badly affect the mechanical resistance of the balloon.

SUMMARY OF THE INVENTION

In these conditions, it is the object of the present invention to solve the technical problem consisting in providing a dilatation catheter of novel design, which will ensure a large body fluid flowing section, which can be produced easily on an industrial scale, and which is relatively easy to use.

The solution, according to the invention, for solving this technical problem, consists in a dilatation catheter, designed to be inserted in a canal of the body, particularly in a blood vessel, of the type comprising:

an outer tubular element comprising a distal part and a proximal part, provided at the level of its distal part with a radially deformable portion comprising a balloon, and on either side of said balloon with at least one orifice communicating with said body canal and allowing the fluid flowing in the body canal to flow through said outer tubular element;

an inner tubular element, situated inside said outer tubular element, and allowing the passage of a guide;

a micro-tube, placed preferably inside said outer tubular member, issuing at one end inside said balloon and connected at its other end to a fluid supply source in order to enable the inflating and deflating of said balloon, characterized in that:

said balloon has an outer wall designed to come into contact with the inner wall of said body canal, while in position of use; and an inner wall fixed in tight manner to said outer wall and adapted to define therewith, while in the position of use, an inner annular cavity;

end in that it further comprises a support element shaped so as to hold said inner wall of the balloon, in position of use, while allowing the body fluid to flow in the space between said inner element and the inner wall of the balloon.

Thus, the novelty of the present invention, over the prior art, resides in the fact that by using a balloon with two walls, associated to a suitable support means, a great part of the catheter section comprised between the inner wall of the balloon and the inner tubular element through which passes the guide, is cleared, this enabling a virtually normal flow of the fluid to be maintained in the body canal.

Such a catheter can therefore be kept in position of use in the body canal for a very long time, and long enough for the normal flowing section of the duct, restored by suitable treatments known in the art and recalled hereinabove, to last.

The expression "position of use" as used in the present description an claims designates the stenosis treatment position in which the balloon is inflated.

BRIEF DESCRIPTION OF THE DRAWINGS

The invention will be more readily understood and other advantages and characteristics thereof will become clearer on reading the following detailed description given with reference to the accompanying drawings given by way of example and non-restrictively, illustrating two currently preferred embodiments of the invention, in which drawings.

DETAILED DESCRIPTION OF PREFERRED EMBODIMENTS

In the following description, the body canal chosen by way of example is a blood vessel, not shown, such as, in particular, a coronary artery.

Moreover, the word "front" will designate the distal part of an element and the word "rear" will designate its proximal part.

FIGS. 1 to 7 therefore illustrate the distal part of a dilatation catheter according to a first embodiment of the invention. This catheter comprises an outer tubular element having a distal part and a proximal part, not shown, and an inner tubular element 1 situated inside said outer tubular element, in concentric or eccentric manner (see FIG. 7).

Figure 1:
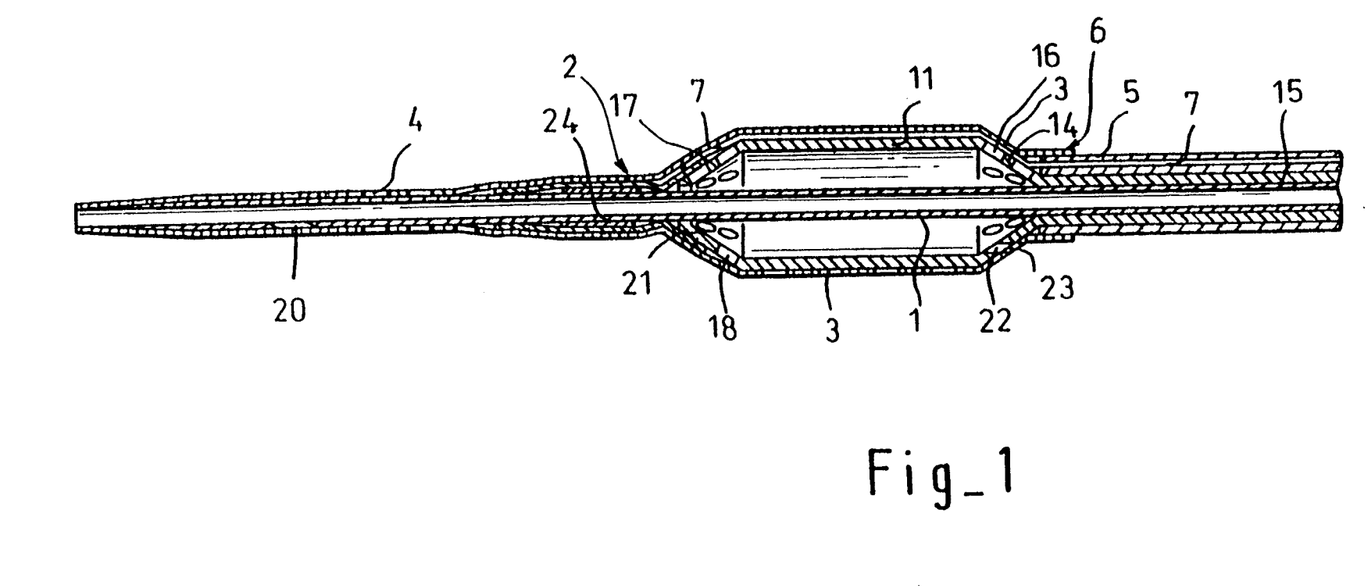
FIG. 1 is a partial longitudinal section of a dilatation catheter according to a first embodiment of the invention before the balloon is inflated.

The inner tubular element 1 has a substantially circular cross-section and allows the passage of a guide generally produced in the form of a wire. Said guide is meant to help positioning the dilatation catheter beyond the distal end of the guide catheter, not shown.

The inner tubular element 1 can be produced for example in a material such as a semi-rigid thermoplastic, for example a polyethylene, a polyamide, a polyurethane or a Pebax ® type copolymer sold by the company Atochem.

The outer tubular element comprises, at the level of its distal part, a radially deformable portion comprising an inflatable balloon 2, and on either side of that balloon, at least one orifice, 3 (upstream) and 4 (downstream), which communicates, while in position of use, with the blood vessel in which the catheter is inserted, thereby allowing the blood flowing in the vessel to pass inside the outer tubular element.

In the example illustrated in the Figures, the outer tubular element comprises a flexible tube 5 on the front part of which is fixed, in tight manner, for example, by heat-bonding or by adhesive means, a part forming sheath, radially deformable and designated by the general reference 6, which is joined to the balloon 2. The balloon 2 can be integrated to the sheath 6, such as in the illustrated example, or fixed thereon.

In the illustrated embodiment, the part forming sheath 6 is fixed in tight manner by its front part of general cylindrically conical shape, while in position of use, to the inner tubular element 1 of which the front part extends beyond the front end of the outer tube 5.

According to a variant, the part forming sheath 6 can be integrated, i.e. produced in one piece with the outer tubular element. In this case, said latter will have a length substantially equal to that of the inner tubular element 1.

The tube 5 will be produced for example in a material such as that used for producing the inner tubular element 1.

The balloon 2 can be produced in a material such as a cross-linked polyethylene, a polyamide or a polyethylene terephtalate, all three being bi-orientated. Said materials are described in the prior art.

The deformable sheath 6 can be produced in the same material as the balloon 2 or in a material compatible therewith.

The outer tubular element comprises a substantially longitudinal micro-channel or micro-tube 7, issuing at its front end inside the balloon 2 and connected at its other end to a fluid supply source, not shown, enabling the balloon 2 to be inflated and deflated.

The micro-channel or micro-tube 7 can be produced for example in a material such as that used for producing the tube 5.

The balloon 2 comprises an outer wall 8 of generally cylindrical shape, when in position of use, said wall being designed to come into contact with the inner wall of the vessel by crushing the deposits causing the stenosis. The balloon 2 further comprises an inner wall 9 fixed laterally in tight manner to the outer wall 8 and defining therewith an inner cavity 10.

Figure 2:
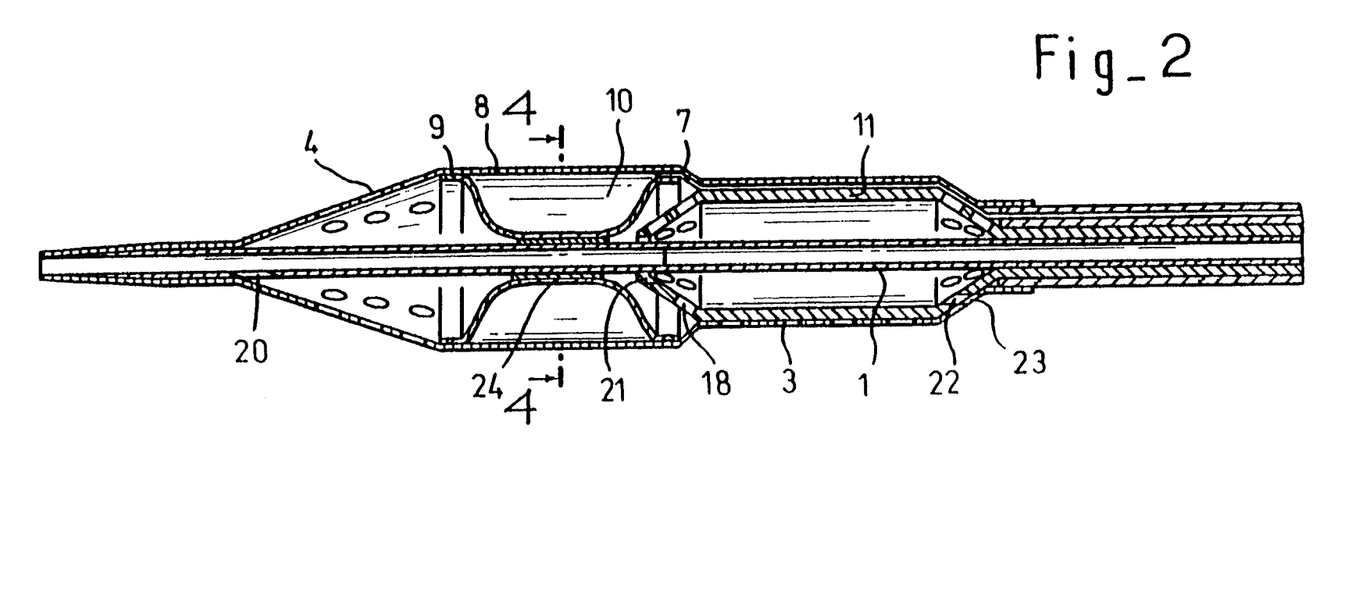
FIG. 2 is a view similar to FIG. 1 of the same catheter, during dilatation of the stenosis.
Figure 4:
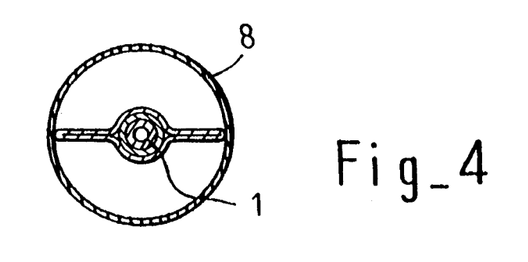
FIG. 4 is a cross-sectional view along line IV—IV of FIG. 2.
Figure 5:
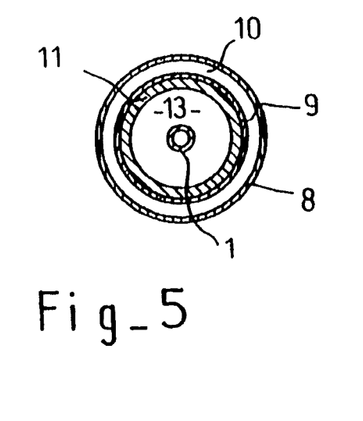
FIG. 5 is a cross-sectional view along line V—V of FIG. 3 taken at the level of the balloon.
Figure 6:
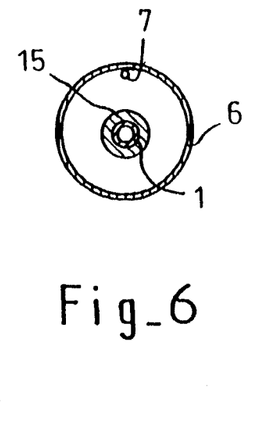
FIG. 6 is a cross-sectional view along line VI—VI of FIG. 3 taken upstream of the balloon.
Figure 7:
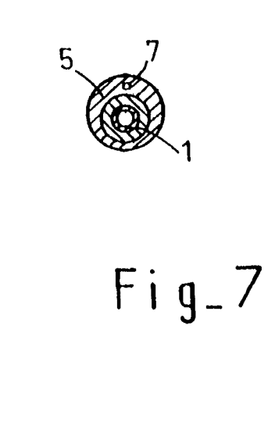
FIG. 7 is a cross-sectional view along line VII—VII of FIG. 3 taken at the level of the proximal part of the catheter.

When the balloon 2 is inflated, the inner wall 9 collapses under the effect of pressure (see FIGS. 2 and 4).

It is thus possible to achieve the dilatation of the stenosis in conventional manner.

It is also possible, and this is the basis of the present invention, to give to the inner cavity 10 an annular shape of substantially rectangular cross-section, by providing a support element for supporting the inner wall 9 designed to recover the stresses caused by the pressure inside the balloon and to create a wide hole for the passage of the body fluid.

According to this first embodiment of the invention, said support element comprises a sleeve 11 of generally cylindrical shape, and of which the length is substantially equal to that of the balloon 2.

The sleeve 11 is movable longitudinally between a rest position, in which it is situated upstream of the balloon 2 (FIG. 2) and a work position in which it supports and holds the inner wall 9 of the balloon 2 (FIG. 3) while moving it apart from the tubular element 1, thereby creating an elongated hole 13 for the passage of the blood inside the sleeve.

Obviously, it is possible, by altering the dimensions of the balloon 2 (notably the width of the inner cavity 10), to obtain a wide hole 13.

The sleeve 11 is connected, at its rear end, via a conical wall 14, to a sliding tube 15 of substantially circular cross-section, of which the inner diameter is slightly greater than the outer diameter of the tubular element 1 and the outer diameter is less than the inner diameter of the tube 5. Consequently, the tube 15 can move in guided manner along the tubular element 1, thereby forming a means controlling the longitudinal movement of the sleeve 11.

The conical wall 14 comprises one or more orifices 16 allowing the flow inside the sleeve 11 of the blood coming from the blood vessel through orifices 3 situated upstream of the balloon 2 (see arrows F).

Figure 3:
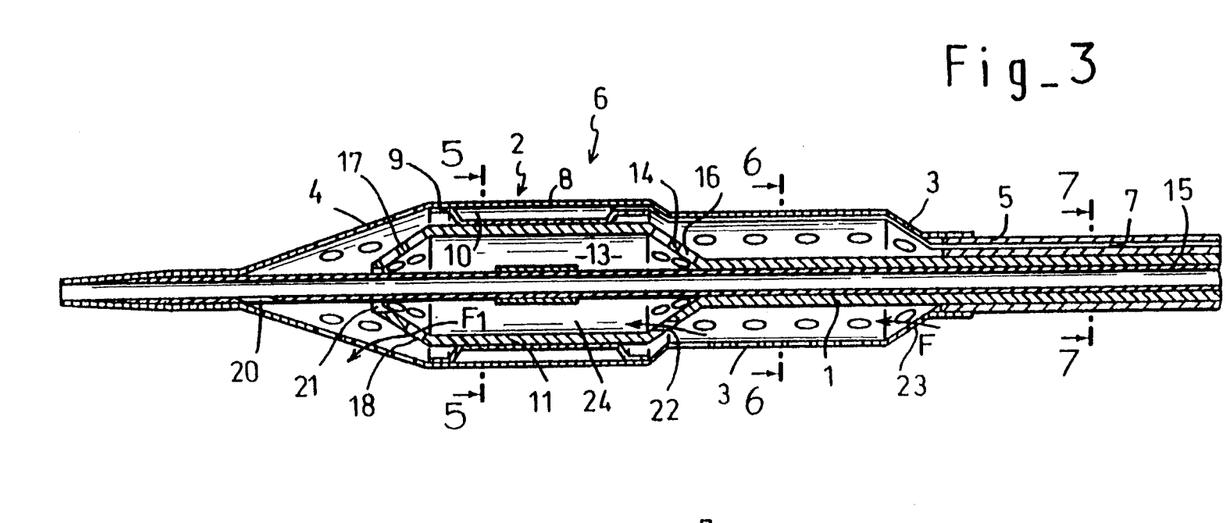
FIG. 3 is a view similar to FIG. 1 of the same dilatation catheter showing the inflating being kept up and the free flow of the body fluid.

Preferably, the sleeve 11 is provided at its front end, with a conical wall 17, for easily placing the sleeve 11 in its work position illustrated in FIG. 3.

The conical front wall 17 comprises one or more orifices 18, which cooperate with the orifices 4 situated downstream of the balloon 2 to ensure the passage of the blood into the sleeve 11 and towards the part of the blood vessel situated downstream of the balloon (see arrows F₁).

The sleeve 11 can be produced in one piece with the conical front wall 17, and the conical rear wall 14 and the tube 15 can be made for example in a material such as that used for the tube 5 or in fluoroethylene propylene (F.E.P.) showing good friction resistance.

In FIGS. 1 to 3, the reference numerals 20, 21, 22, 23 designate orifices provided, respectively, in the inner tubular element 1, in the rear wall 14 of the sleeve 11 and in the rear part of the sleeve 6, for the lateral passage of a guide.

Orifices 22 and 23 are in substantially facing relationship when the sleeve 11 is in rest position as illustrated in FIG. 2.

The reference numeral 23 designates a metallic radiopaque element the function of which is to indicate the position of the balloon 2 by radioscopy. This element is extensively described in the prior art. In the illustrated example, said element is produced in the form of a ring placed around the inner tubular element 1.

Figure 8:
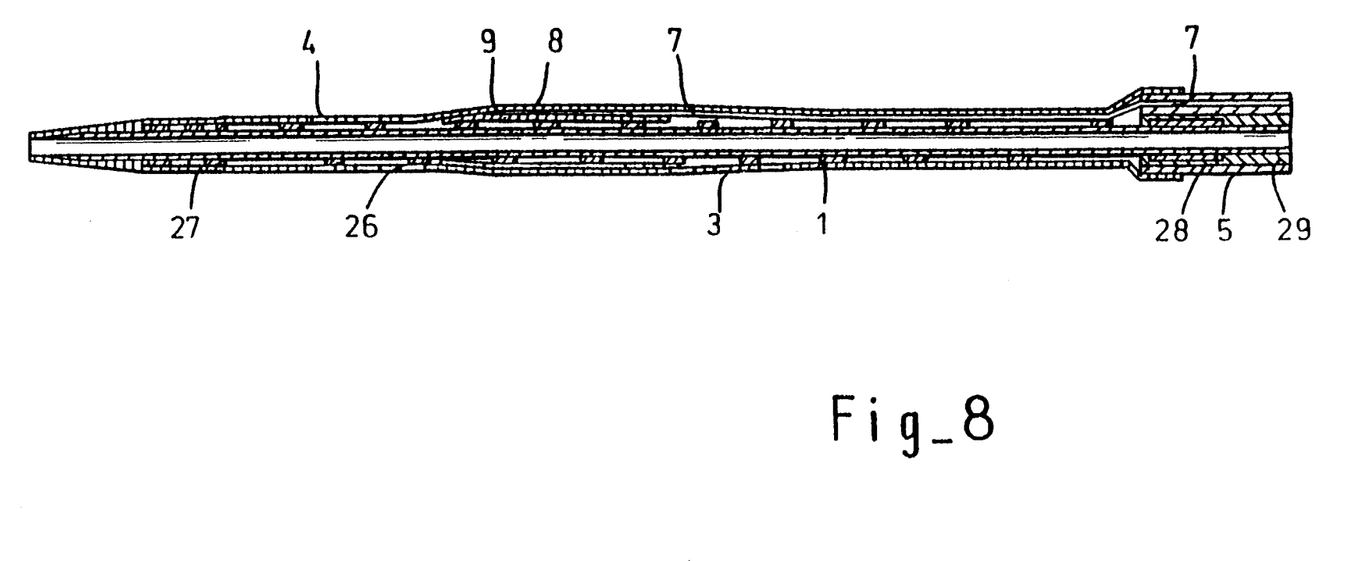
FIG. 8 is a partial longitudinal section of a dilatation catheter according to a second embodiment of the invention, before the balloon is inflated.
Figure 9:
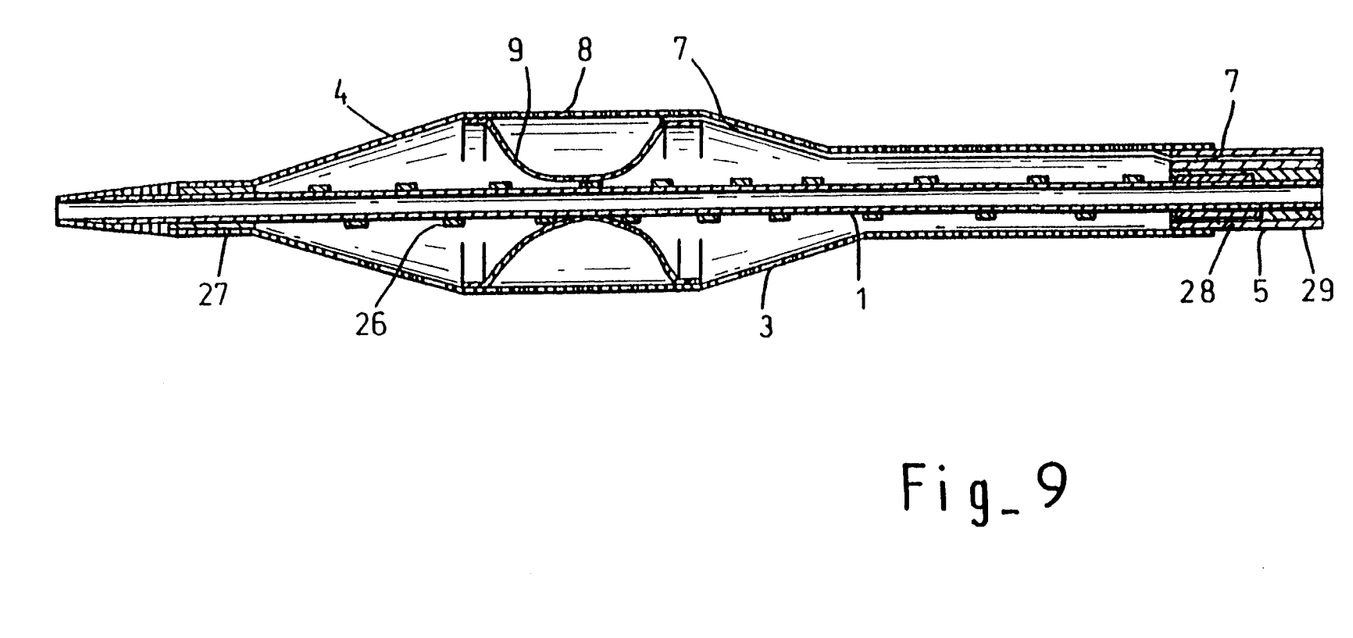
FIG. 9 is a view similar to FIG. 8 of the same catheter during dilatation of the stenosis.
Figure 10:
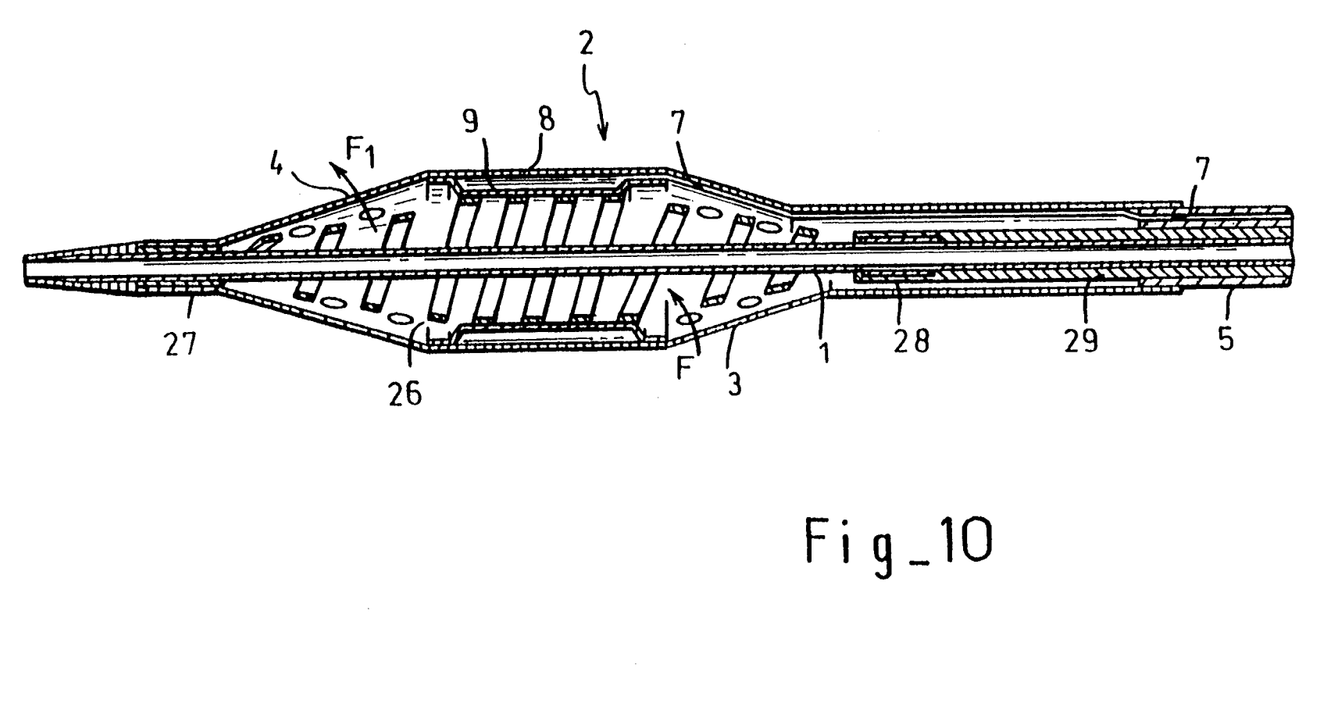
FIGS. 10, 11 and 12 are views similar to FIG. 9 of the same catheter showing the inflating being kept up by a spring-forming element mash and grid, respectively, with free flow of the body fluid.

FIGS. 8 to 10 show the distal part of a dilatation catheter according to a second embodiment of the invention.

The elements which are identical to those described with reference to the first embodiment have been given the same reference numerals.

In this second embodiment of the invention, said support element comprises a helical spring 26 of which the front end 27 situated downstream of the balloon 2 is fixed, for example by being bonded to the inner tubular element 1, and of which the rear end 28 is mobile, for example by being fixed in a recess provided in a sliding tube 29 similar to the tube 15 described with reverence to the first embodiment.

The spring 28 is capable of occupying an extended position, illustrated in FIGS. 8 and 9, reached by pulling the rear end 28 and a rest position illustrated in FIG. 10 in which its spires situated at the level of the balloon, support and hold the inner wall 9 of the balloon in position, while moving it apart from the tubular element 1 and in doing so creating a wide hole for the blood to flow through.

The outer diameter of the spires of spring 26 is, in rest position, greater than the outer diameter of said spires in extended position.

The blood can thus flow through the end of the dilatation catheter, entering through orifices 3 and coming out through orifices 4.

Said extended position is obtained by simply pulling on the sliding tube 29.

The spring 26 can be produced for example as a stainless steel wire, for example of norm A.I.S.I. 305, preferably of rectangular cross-section, or in a metal alloy with shape memory and high elasticity, such as for example of NITINOL ® type.

Figure 11:
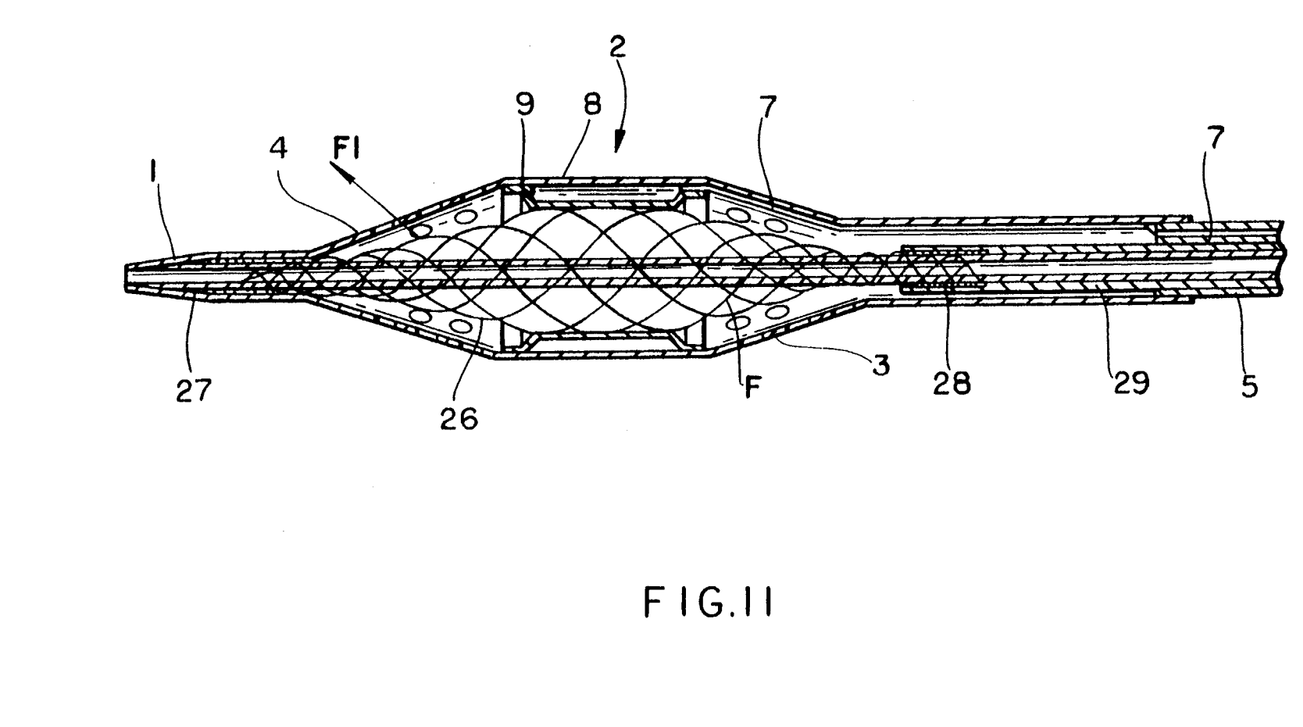
Figure 12:
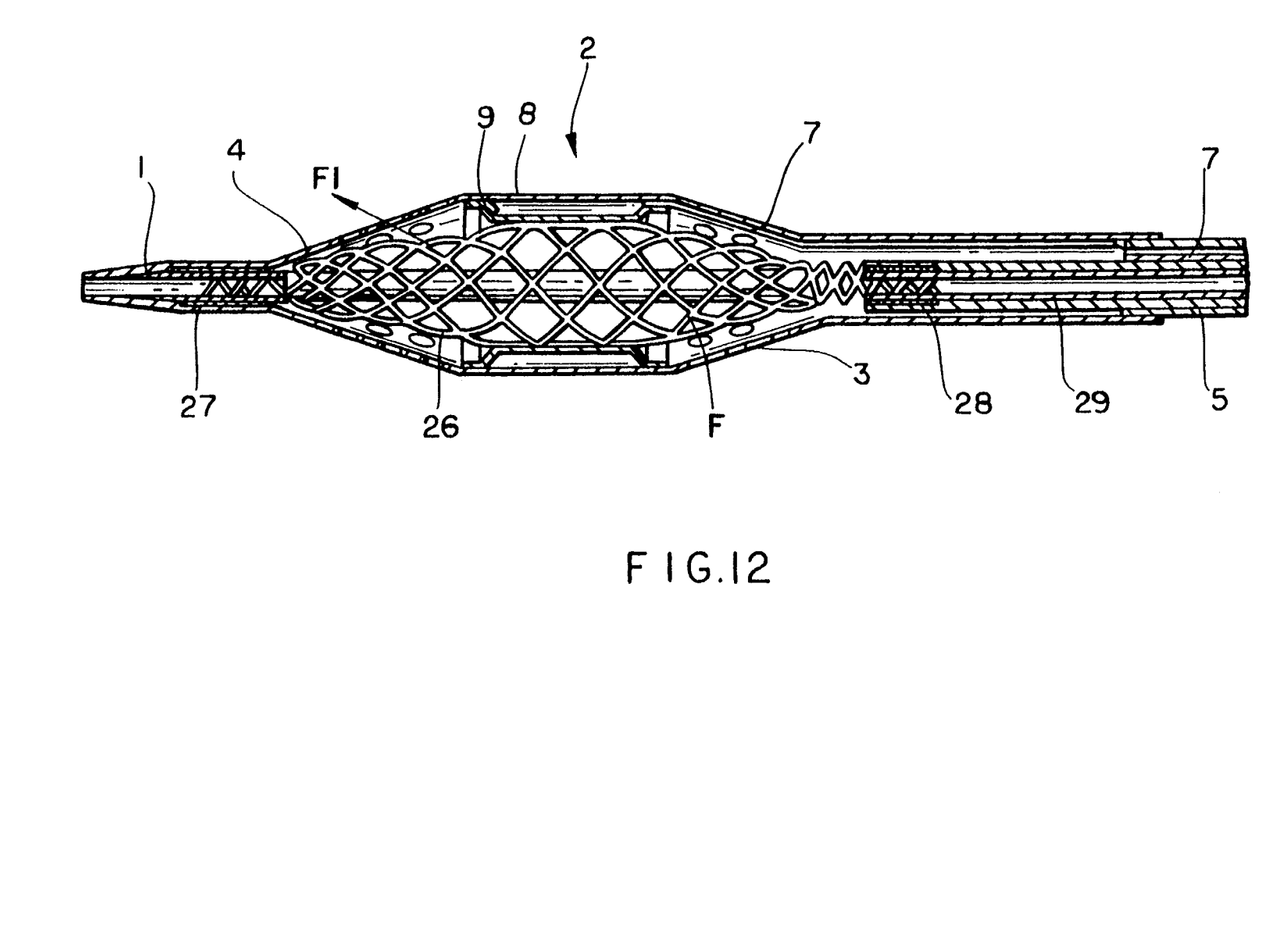

Optionally, said helical spring can be replaced by any structure deformable radially by bringing its ends close together such as a grid (FIG. 12) or a metallic mesh (FIG. 11).

The catheters according to the two embodiments just described hereinabove, are relatively easy to use, by a technique very similar to that described in the prior art.

For example, the catheter is introduced, conventionally, by using a metallic guide, to the level of the stenosis. During this operation, the outer sheath 6 is in folded state as illustrated in FIGS. 1 and 8. The dimensions of the catheter are then quite comparable to those of a conventional dilatation catheter.

Then the balloon 2 is inflated for dilating the stenosis in the conventional way as illustrated in FIGS. 2 and 9.

The balloon 2 is thereafter deflated in order to allow the positioning of the sleeve 11 or of the spring 26.

Then the balloon is inflated a second time to dilate once more the stenosis while allowing a virtually normal blood flow through the catheter (FIGS. 3 and 10, 11 or 12).

The catheter can remain in this last position for a very long time (about several dozens of minutes, if necessary) and thereby offers a long-lasting treatment of stenosis.

What is claimed is:

1. A dilatation catheter, designed to be introduced into a canal of the body, notably a blood vessel, comprising:

an outer tubular element having a distal part and a proximal part, said outer tubular element being provided at the distal part with a radially deformable portion having a balloon and, on either side of said balloon, at least one orifice is formed in fluid communication with said body canal so as to allow the fluid flowing in the body canal to flow through said outer tubular element, said balloon having an outer wall designed to press against the inner wall of said body canal, while in position of use, and an inner wall fixed in tight manner to said outer wall to define therewith, while in position of use, an inner annular cavity;

an inner tubular element, situated inside said outer tubular element, so as to allow the passage of a guide through said catheter;

a micro-tube, connected to said balloon at one end and connectable to a fluid supply source at an other end so that said balloon is in fluid communication with said fluid supply source in order to enable the inflating and deflating of said balloon; and a sleeve positioned between said inner tubular element and outer tubular element, having a generally cylindrical shape, said sleeve having a distal part and a proximal part and being movable longitudinally between a rest position, in which it is situated upstream of the balloon, and a work position, in which it supports and holds the inner wall of the balloon while moving it apart from the inner tubular element to create an elongated hole for the passage of the body fluid inside the sleeve.

2. The dilatation catheter of claim 1, wherein the outer tubular element comprises a flexible tube having a proximal part, and a distal part on which is fixed, in a tight manner, a sheath which is radially deformable and is joined to the inside of the balloon.

3. The dilatation catheter of claim 2, wherein the sleeve is connected at its proximal part, via a conical wall, to a sliding tube of substantially circular cross-section, of which the inner diameter is slightly greater than the outer diameter of the inner tubular element, and the outer diameter is less than the inner diameter of said flexible tube.

4. The dilatation catheter of claim 3, wherein said conical wall comprises one or more orifices allowing the flow inside the sleeve of said body fluid.

5. The dilatation catheter of claim 2, wherein said sleeve comprises at its distal part, a conical wall provided with one or more orifices allowing the body fluid to flow from inside the sleeve towards the part of the body canal situated downstream of the balloon.

6. A dilatation catheter, designed to be introduced into a canal of the body, notably a blood vessel, comprising:

an outer tubular element having a distal part and a proximal part, said tubular element being provided at the distal part with a radially deformable portion having a balloon and, on either side of said balloon, at least one orifice is formed in fluid communication with said body canal so as to allow the fluid flowing in the body canal to flow through said outer tubular element, said balloon having an outer wall designed to press against the inner wall of said body canal, while in position of use, and an inner wall fixed in a tight manner to said outer wall to define therewith, while in position of use, an inner annular cavity;

an inner tubular element, situated inside said outer tubular element, so as to allow the passage of a guide through said catheter;

a micro-tube, connected to said balloon at one end and connectable to a fluid supply source at an other end so that said balloon is a fluid communication with said fluid supply source in order to enable the inflating and deflating of said balloon; and a helical spring, positioned between said inner tubular element and said outer tubular element, having a front end and a rear end of which the front end, situated downstream of the balloon, is fixed, and the rear end is mobile, said spring being capable of occupying an extended position, reached by pulling its rear end, and a rest position in which its spires, situated by the balloon, support and hold the inner wall of the balloon in position while moving it apart from the inner tubular element to create an elongated hole for the body fluid to flow through.

7. The dilatation catheter of claim 6, wherein the rear end of said spring is fixed in a recess provided in a sliding tube of which the inner diameter is slightly greater than the outer diameter of the inner tubular element, and the outer diameter is less than the inner diameter of said flexible tube.

8. A dilatation catheter, designed to be introduced into a canal of the body, notably a blood vessel, comprising:

an outer tubular element having a distal part and a proximal part, said tubular element being provided at the distal part with a radially deformable portion having a balloon and, on either side of said balloon, at least one orifice is formed in fluid communication with said body canal and so as to allow the fluid flowing in the body canal to flow through said outer tubular element, said balloon having an outer wall designed to press against the inner wall of said body canal, while in position of use, and an inner wall fixed in a tight manner to said outer wall to define therewith, while in the position of use, an inner annular cavity;

an inner tubular element, situated inside said outer tubular element, so as to allow the passage of a guide through said catheter;

a micro-tube, connected to said balloon at one end and connectable to a fluid supply source at an other end so that said balloon is in fluid communication with said fluid supply source in order to enable the inflating and deflating of said balloon; and a support element which, in position of use, is located between the balloon and the inner tubular element, said support element having a distal end and a proximal end, and is deformable radially by bringing its ends close together so as to support and hold the inner wall of the balloon in position, while moving it apart from the inner tubular element, to create an elongated hole for the body fluid to flow through.

9. The dilatation catheter of claim 8, wherein said support element has a from of a grid.

10. The dilatation catheter of claim 8, wherein said support element has a from of a mesh.

11. A dilatation catheter, designed to be introduced into a canal of the body, notably a blood vessel, comprising:

an outer tubular element having a distal part and a proximal part, said tubular element being provided at the distal part with a radially deformable portion having a balloon and, on either side of said balloon, at least one orifice is formed in fluid communication with said body canal so as to allow the fluid flowing in the body canal to flow through said outer tubular element, said balloon having an outer wall designed to press against the inner wall of said body canal, while in position of use, and an inner wall fixed in tight manner to said outer wall to define therewith, while in the position of use, an inner annular cavity;

an inner tubular element, situated inside said outer tubular element, so as to allow the passage of a guide through said catheter;

a micro-tube, connected to said balloon at one end and connectable to a fluid supply source at an other end so that said balloon is in fluid communication with said fluid supply source in order to enable the inflating and deflating of said balloon; and a support element which in position of use is located in proximity to said balloon between the balloon and the inner tubular element and which is conformed so as to recover the stresses caused by the pressure inside the balloon and to move said balloon apart from the inner tubular element, thereby creating a space between said inner element and the inner wall of the balloon for the passage of the body fluid.

* * * * *

UNITED STATES PATENT AND TRADEMARK OFFICE
CERTIFICATE OF CORRECTION

PATENT NO. :  5,378,237
DATED      :  January 3, 1995
INVENTOR(S):  Georges Boussignac, etal.

It is certified that error appears in the above-identified patent and that said Letters Patent is hereby corrected as shown below:

On title page, left column, item 73,
"Ingenop" should be -- Ingenor --.

Signed and Sealed this

Twentieth Day of June, 1995

Attest:

BRUCE LEHMAN

*Attesting Officer*    *Commissioner of Patents and Trademarks*